United States Patent
Reiderman et al.

(10) Patent No.: US 6,445,180 B1
(45) Date of Patent: Sep. 3, 2002

(54) NUCLEAR MAGNETIC RESONANCE TOOL WITH ACTIVE RF SPOILER ANTENNA

(75) Inventors: Arcady Reiderman; David Beard, both of Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 0 days.

(21) Appl. No.: 09/605,265

(22) Filed: Jun. 28, 2000

(51) Int. Cl.[7] .................................................. G01V 3/00
(52) U.S. Cl. ......................................................... 324/303
(58) Field of Search ................................ 324/303, 338, 324/300

(56) References Cited

U.S. PATENT DOCUMENTS

| | | | |
|---|---|---|---|
| 4,350,955 A | 9/1982 | Jackson et al. | 324/303 |
| 4,717,877 A | 1/1988 | Taicher et al. | 324/303 |
| 5,055,787 A | 10/1991 | Kleinberg et al. | 324/303 |
| 5,153,514 A * | 10/1992 | Griffin et al. | 324/303 |
| 5,488,342 A | 1/1996 | Hanley | 335/306 |
| 5,594,343 A * | 1/1997 | Clark et al. | 324/338 |
| 5,646,528 A | 7/1997 | Hanley | 324/303 |
| 5,831,433 A | 11/1998 | Sezginer et al. | 324/303 |
| 6,023,164 A | 2/2000 | Prammer | 324/303 |
| 6,255,818 B1 * | 7/2000 | Heaton et al. | 324/303 |
| 6,255,817 B1 * | 7/2001 | Poitzsch et al. | 324/303 |

FOREIGN PATENT DOCUMENTS

| EP | WO 02/01255 | * 3/2002 |
|---|---|---|
| WO | WO 99/42858 | 8/1999 |

* cited by examiner

*Primary Examiner*—Edward Lefkowitz
*Assistant Examiner*—Tiffany A. Fetzner
(74) *Attorney, Agent, or Firm*—Madan, Mossman & Sriram, P.C.

(57) ABSTRACT

A novel nuclear magnetic resonance (NMR) probe design for operating in a bore hole to obtaining the NMR characteristics of a region of interest adjacent the bore hole, characterized by a main RF antenna, a magnet, and a spoiler antenna. The spoiler antenna performs as an active shield for generating a resultant RF field that forcefully mismatches the static magnetic field inside the bore hole and substantially does not affects the RF field or antenna sensitivity in the region of interest.

44 Claims, 6 Drawing Sheets

NUCLEAR MAGNETIC RESONANCE TOOL WITH ACTIVE RF SPOILER ANTENNA

CROSS-REFERENCE TO RELATED APPLICATIONS

This application is related to U.S. patent application Ser. No. 09/605,463 of Reiderman et al. filed on Jun. 28, 2000 the contents of which are fully incorporated herein by reference.

FIELD OF THE INVENTION

The present invention relates generally to the field of nuclear magnetic resonance (NMR) tools for oil well logging and in particular to an active RF spoiler antenna for reducing the NMR signal from the bore hole in a side looking NMR tool.

BACKGROUND OF THE RELATED ART

NMR well logging instrument typically include a permanent magnet to induce a static magnetic field in the earth formations and a transmitting antenna, positioned near the magnet and shaped so that a pulse of radio frequency (RF) power conducted through the antenna induces an RF magnetic field in the earth formation. The RF magnetic field is generally orthogonal to the static magnetic field. After an RF pulse, voltages are induced in a receiving antenna by precessional rotation of nuclear spin axes of hydrogen or other nuclei about the static magnetic field. The precessional rotation occurs in an excitation region where the static magnetic field strength corresponds to the frequency of RF magnetic field. A sequence of RF pulses can be designed to manipulate the nuclear magnetization, so that different aspects of the NMR properties of the formation can be obtained. For NMR well logging the most common sequence is the CPMG sequence that comprises one excitation pulse and a plurality of refocusing pulses.

A "side-looking" NMR tool is sensitive to NMR excitation on one side of the tool and less sensitive to NMR excitation on the other side. The more sensitive side of the tool is typically pressed against the side wall of a borehole adjacent a formation, thereby providing minimum separation between the NMR tool's RF field generating assembly and the formation volume of NMR investigation. The less sensitive side of the tool is thus exposed to the bore hole. This operational NMR technique is most effective when the borehole diameter is much greater than the diameter of the NMR tool.

Typically, side-looking NMR tools set up static and RF magnetic field distributions in a particular relationship to achieve maximum NMR sensitivity on one side of the NMR tool. These conventional side looking NMR techniques are well known in the art, as taught in the following patents: U.S. Pat. No. 5,055,787, Kleinberg et al., entitled Borehole Measurements Of NMR Characteristics Of Earth Formation; U.S. Pat. No. 5,488,342, Hanley, entitled Magnet Assembly For NMR; U.S. pat. No. 5,646,528, Hanley, entitled Magnet Assembly; and WO 9942858, Prammer et al., entitled Eccentric NMR Well Logging Apparatus And Method.

The '787 patent teaches a side-looking NMR tool which generates a static magnetic field which results in a sensitive volume on only the front side of the tool. The sensitive region in front of the '787 tool generates a field having a substantially zero gradient, while the region behind the '787 tool has a relatively large gradient field. Consequently, the volume of the sensitive NMR region in front of the tool is much larger and contributes more significantly to the composite NMR signal, than does the NMR region behind the tool. The '787 patent technique, however, is only practical when the sensitive volume in front of the tool is very close to the tool and therefore limits the available depth of NMR investigation. The '787 tool design also requires a substantially zero gradient in the sensitive volume. Such a zero gradient is not always desirable, however, in NMR well logging, as a number of associated NMR techniques depend upon having a finite, known gradient within the NMR sensitive volume.

The '342 patent teaches a NMR tool technique which provides a homogeneous region localized in front of the tool. The '342 tool design overcomes the disadvantageous requirement of the sensitive volume being undesirably close to the NMR tool. The '342 tool, however, suffers because the sensitive volume is not elongated along the longitudinal axis of the NMR tool or bore hole axis, which causes unacceptable errors due to motional effects.

Another possibility would be to design a NMR tool that generates a static field so that the resonant region behind the tool is so far away that it never encroaches into any reasonably expected borehole diameter. This, however, would either require stronger magnets than are currently being used, or a lowering of the tool operating frequency. Stronger magnets are undesirable because they increase the cost, weight and size of the instrument. Moreover, the stronger magnets may attach to the well bore casing, making it difficult or impossible to pass the NMR tool through the casing to the borehole. Moreover, lowering the tool frequency is not desirable, because it lowers the signal-to-noise ratio for the NMR measurement.

A more effective way to reduce the signal from the region behind the tool is with the use of an RF shield. This is done to a great extent in U.S. Pat. No. 5,055,787, cited above, where the tool body effectively shields the antenna; and discussed in the patents U.S. Pat. No. 5,646,528 and WO99/42858. The passive RF shield is typically positioned as far as possible from the front region in order not to spoil NMR tool sensitivity in the desired region and as close as possible to the back region for maximum effectiveness. It can be seen therefore that the effectiveness of the passive shield will eventually be limited by the diameter of the tool. If we can not achieve sufficient attenuation with a shield inside the tool we will have to adopt one of the following undesirable options: use the large magnet to move the rear region further away; reduce the signal from the front region; or place a shield outside the tool. Thus, neither approach presents a practicable solution.

SUMMARY OF THE INVENTION

The present invention provides an active RF shield, or RF spoiler antenna which overcomes the limitations of the known side looking NMR tool designs described above. It is an object of the present invention to minimize NMR sensitivity behind the tool where the NMR signal from the bore hole tends to erroneously contribute to the received NMR signal. The spoiler antenna provides a substantial reduction in sensitivity of a side-looking NMR tool in the region in the bore hole without a reduction in sensitivity in the desired region of investigation and without the necessity of larger magnets, larger tool diameters, or external shields.

In accordance with the present invention, a side-looking NMR probe comprises a magnet for inducing a static magnetic field in the region of interest; a first antenna assembly for inducing a radio frequency (RF) magnetic field and receiving signals from the region of interest; and a second antenna assembly for compensating the RF magnetic field so that the resultant RF field forcefully mismatches the static magnetic field inside of the bore hole in order to reduce contributions from the bore hole to the sensed NMR signal. The second antenna is preferably active only during a transmit period of the first antenna. In another preferred embodiment the second antenna is active only during the excitation RF pulse and not active during refocusing pulses. In a preferred embodiment the magnet has a magnetic dipole moment perpendicular to a line which passes through the effective centers of the first antenna assembly dipole moment and the second antenna assembly dipole moment. The first and the second antennas preferably comprise a soft magnetic core.

In specific embodiments of the invention the NMR tool includes driving circuits which switch the second antenna in and out of the circuit as required. If the second antenna is switched in and out of the antenna circuit, it will change the inductance of the circuit, and hence the resonant frequency. In a specific embodiment the inductance of the first antenna is at a level where this change is small, and can be ignored. In an alternative embodiment a dummy inductor is employed to maintain the resonant frequency of the first antenna.

BRIEF DESCRIPTION OF DRAWINGS

In the discussion of the drawings, like numbers refer to like parts, even though they may appear in different figures.

DETAILED DESCRIPTION OF THE PREFERRED EMBODIMENT

Figure 1:
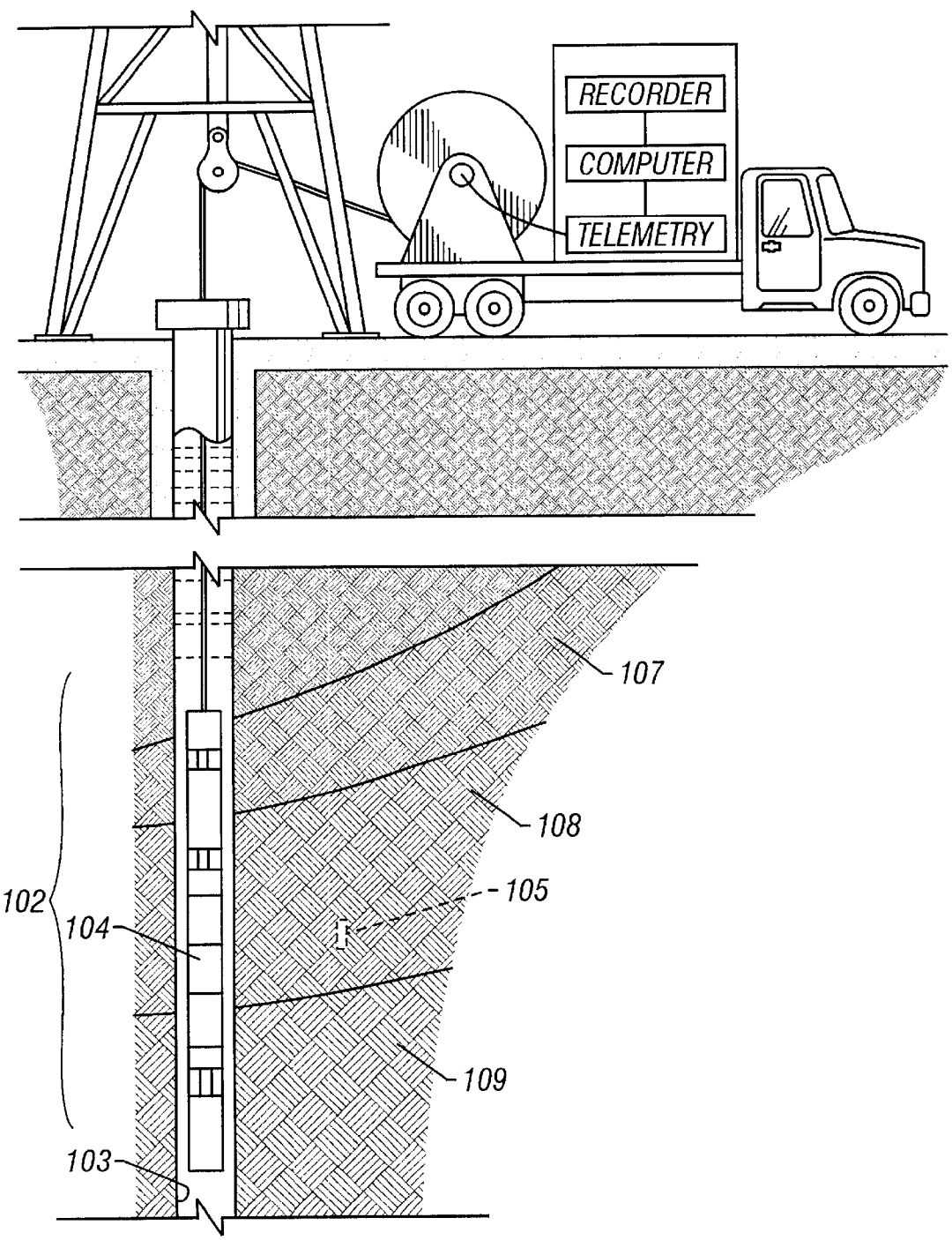
FIG. 1 shows a side-looking well logging tool as it is typically used in a bore hole penetrating earth formation.

FIG. 1 shows a well logging NMR tool 102 deployed in bore hole 103 penetrating earth formations 107,108,109 for making measurements of properties of the earth formations. The borehole 103 in FIG. 1 is typically filled with a fluid known in the art as "drilling mud". The side-looking tool has antenna assembly 104 for generating NMR excitation pulses in a region of investigation 105 and receiving NMR signal from the region 105 in formation 107,108,109 adjacent bore hole 103. The region of investigation 105 is to one side of the tool.

Figure 2:
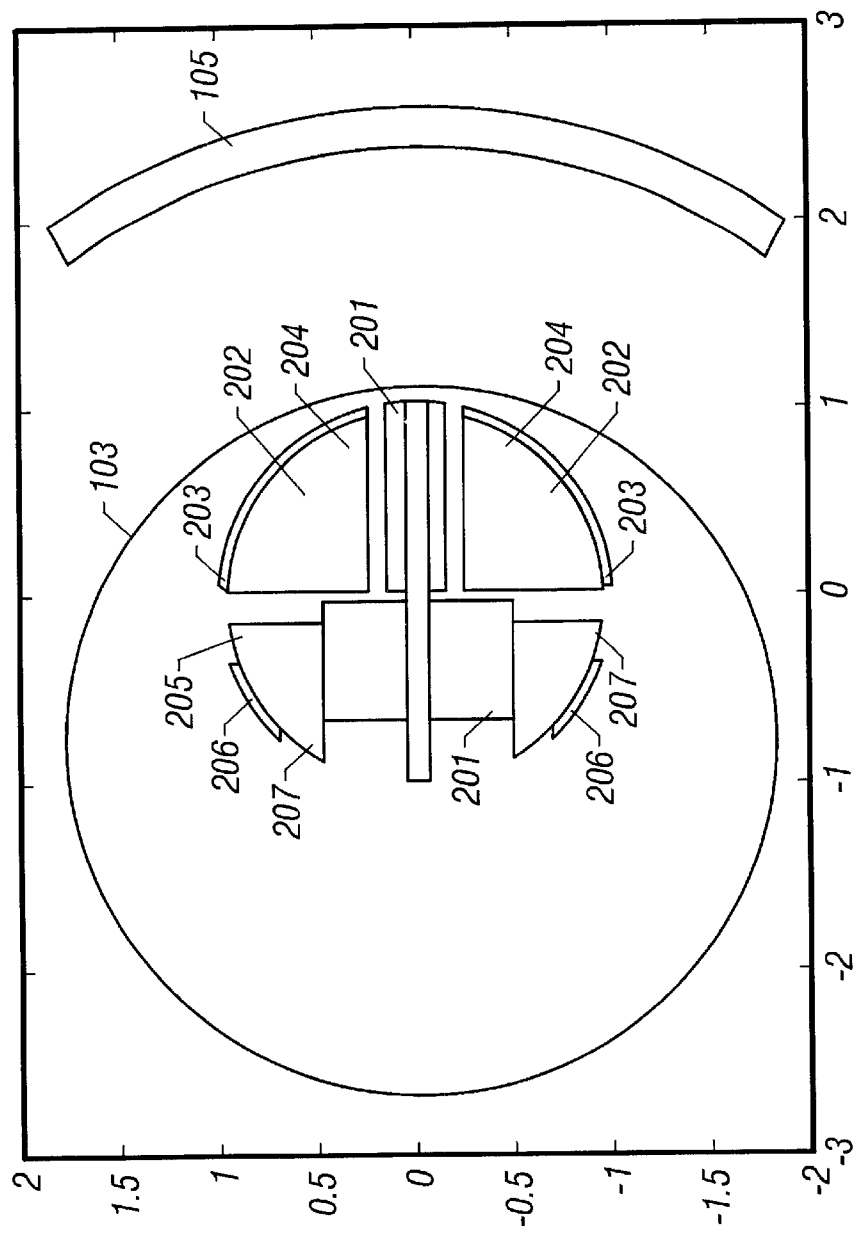
FIG. 2 is a schematic of a preferred embodiment of the RF spoiler antenna illustrating the principle of the present invention.

FIG. 2 shows the cross-section of the preferred NMR probe perpendicular to the longitudinal axis of the NMR tool, which is typically parallel to the bore hole 103 axis. The magnet assembly 201 induces a required distribution of a static magnetic field in a region of interest 105 in the formation, adjacent bore hole 103. The main RF antenna assembly 202 generates a RF magnetic field in the region of interest in the transmit mode and receives the NMR signal from the excitation region of the formation (the region of interest) in the receive mode. The first antenna assembly, the main RF antenna comprises an antenna winding 203 and a soft magnetic core 204 to improve the first antenna efficiency in both the transmit and receive modes. The second antenna assembly 205 serves as an active spoiler comprising winding 206 and preferably a soft magnetic core 207 to improve the efficiency of the spoiler. The antenna and spoiler winding can be either one turn flat wire or multi-turn winding.

Figure 3:
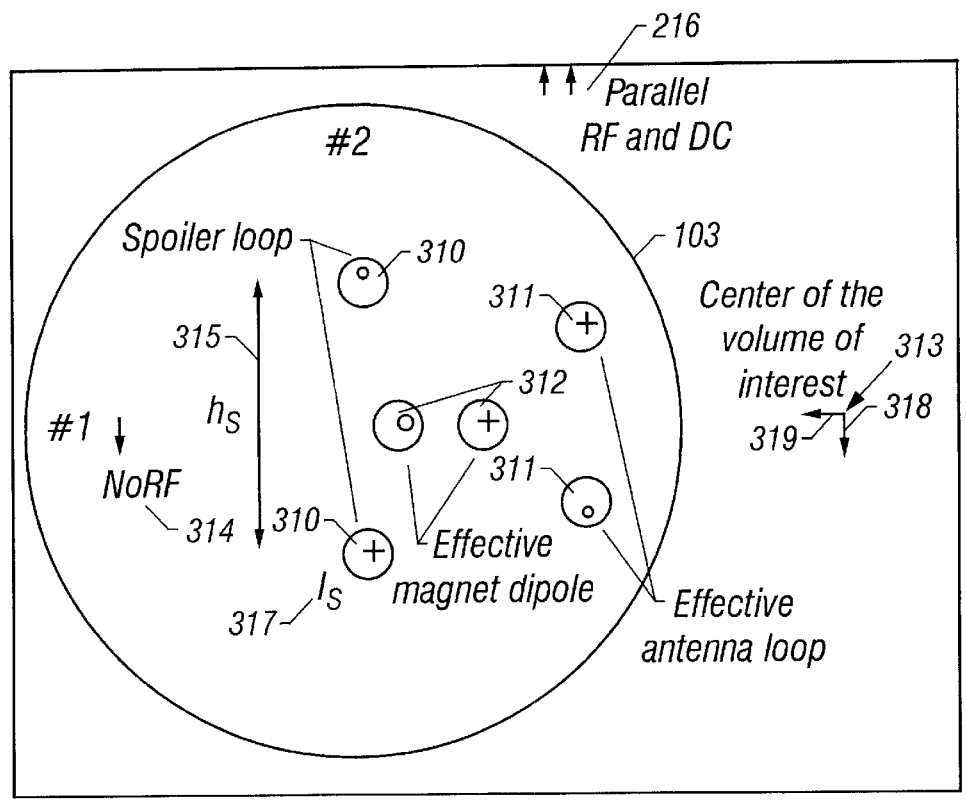
FIG. 3 illustrates a cross sectional view of a preferred embodiment of the present invention.

FIG. 3 illustrates a basic concept of the preferred active spoiler. Shown in the FIG. 3 are the effective antenna current loop 311 representing the main RF antenna, effective currents 310 representing magnet dipole 312 and the effective current loop 310 representing the spoiler antenna. The spoiler antenna current $I_s$ 317 and the effective loop size $h_s$ 315 are varied to achieve the NMR signal spoiling effect in the bore hole. To better understand the spoiler effect we consider, for example, three points 313, 314 and 316 of the DC magnetic field isoline. The point 313 represents the center of the region of investigation where the static magnetic field 318 of the effective magnet dipole is perpendicular to the RF magnetic field 319 of the antenna assembly. Points 314 and 316 are located in the bore hole where the parasitic NMR signal from drilling mud could be generated. The spoiler antenna current 317 and the effective loop size 315 can be adjusted to substantially annul the RF field in vicinity of the point 314 and also to spoil NMR excitation condition near the point 316 where the RF and DC magnetic fields are parallel. Since the effective antenna loop 311 is substantially closer to the region of investigation than the spoiler 310, the effect of the spoiler on the RF field at the region of investigation is reasonably small. An important advantage of the preferred probe design using active RF spoiler antenna is that the spoiler 310 can be disconnected from the main antenna during the receive period of the antenna operation. There is no sensitivity reduction due to RF spoiler in this case.

Figure 4:
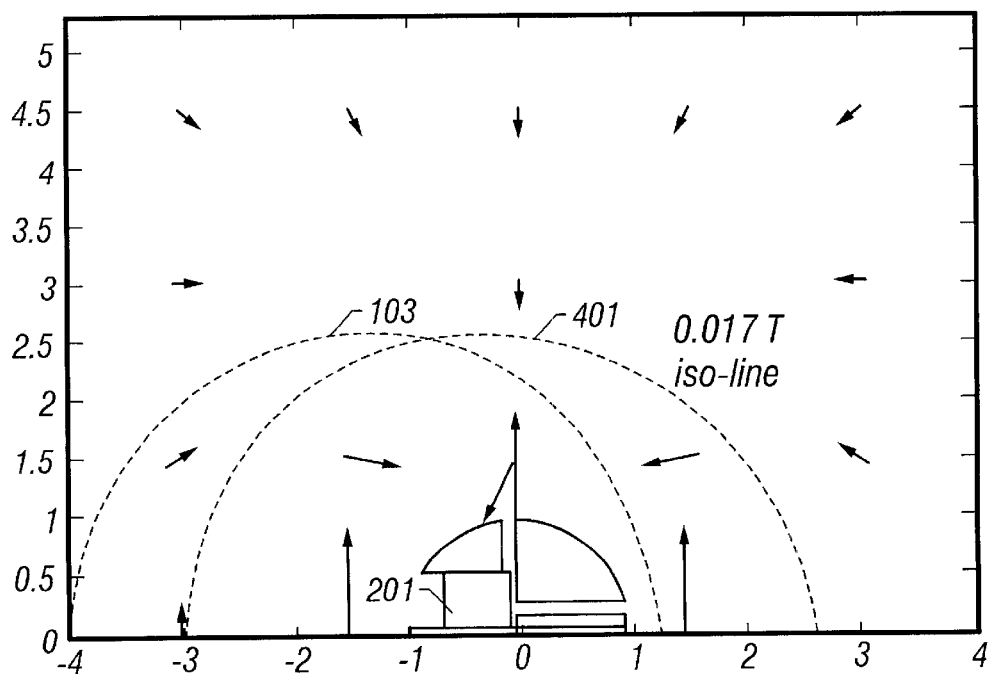
FIG. 4 illustrates a DC field isoline entering the bore hole.

FIG. 4 shows results of computer simulation for the static magnetic field. The DC magnetic field isoline 401 is presented illustrating that a portion of the isoline enters the bore hole 103, which creates the potential for NMR excitation in the bore hole. Thus, there is a need for RF spoiler to prevent NMR excitation in this region. The degree to which each portion of the sensitive volume contributes to the received NMR signal is controlled by the relative coupling, (B/I) of the RF antenna in the sensitive volume. The ratio, B/I represents the magnitude of flux density, B generated by the RF antenna with current, I. In the NMR tool transmit mode, the ratio B/I for the transmitter antenna determines the angle of rotation of the magnetization in the sensitive volume or the NMR region of investigation. In the receive mode, the ratio, B/I of the RF receiver antenna determines, in accordance with the reciprocity theorem, the amplitude of the received signal.

Figure 5:
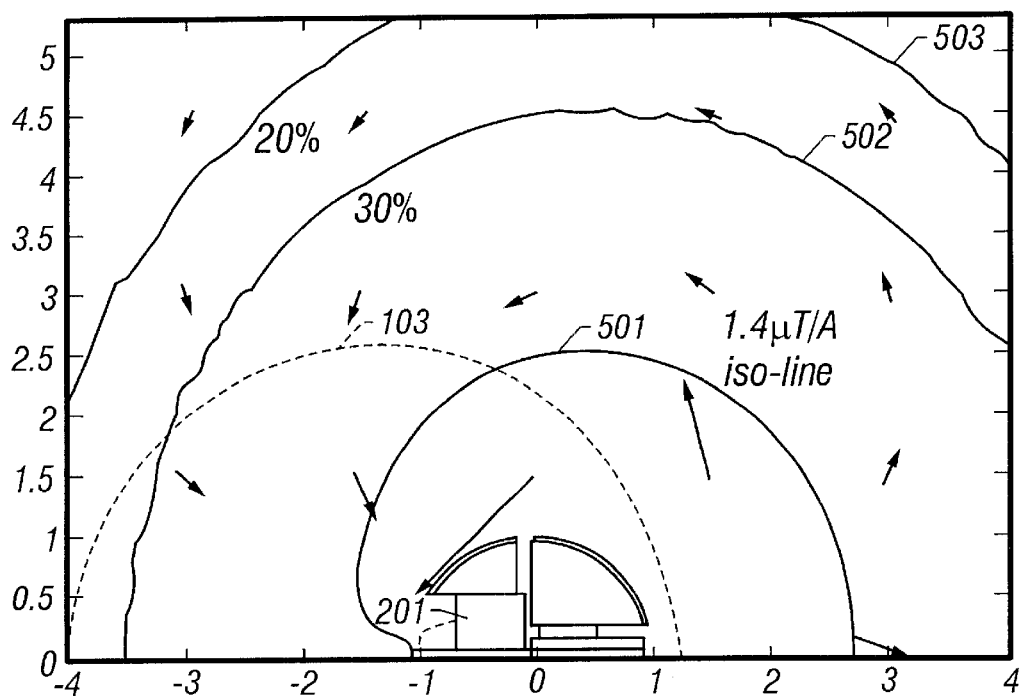
FIG. 5 illustrates the RF magnetic field for a NMR tool with an active spoiler switched out of the antenna circuit.

FIG. 5 illustrates RF magnetic field intensities 501, 502 and 503 for a NMR tool with zero current in the active spoiler. As shown in FIG. 5, more than 30 percent of the main RF field is present in the bore hole along with the DC field isoline shown in FIG. 4, thereby creating significant NMR excitation conditions in the bore hole.

Figure 6:
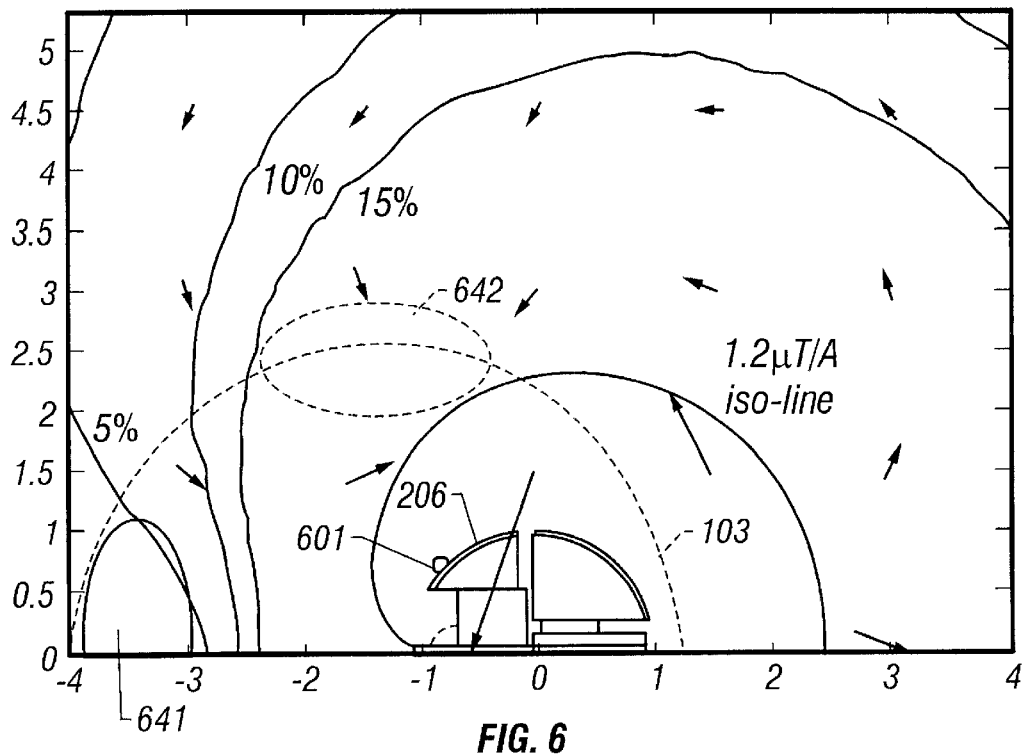
FIG. 6 illustrates a RF magnetic field intensities for a preferred embodiment of the present invention with an active spoiler RF antenna switched in the antenna current.

Turning now to FIG. 6, a preferred embodiment of the invention is shown with the active spoiler RF antenna having the spoiler current intensity 45% of the current in the main antenna. As shown in FIG. 6, the RF field near the DC field iso-line inside the bore hole 103 is substantially reduced compared to that shown in FIG. 5. The RF field is close to zero at the region 641 and substantially parallel to the DC field in region 642, which prevents operable conditions for NMR excitation in the bore hole. The spoiler current, $I_s$ 601 which drives the spoiler RF antenna is preferably adjusted so that the polarity or phase of the effective RF magnetic field alters as we follow the excitation region inside the borehole. A zero integral of the effective RF field 641 over the borehole excitation arc serves as an approximate criterion for adjustment of the spoiler current, $I_s$ 601. A calibration procedure using borehole fluid as the only source of the NMR signal can be employed to minimize the bore hole signal by adjusting the spoiler current.

Comparison of the RF field intensity at the region of investigation in FIGS. 5 and 6 show that the RF field reduction in the region of investigation due to spoiler is from 1.4 $\mu$T/A to 1.2 $\mu$T/A that is about 15%. Since the spoiler is preferably connected to the main antenna only in transmit mode, this reduction does not affect the sensitivity and the signal-to-noise ratio. The only consequence of the reduction of RF field in the region of investigation due to the spoiler is a minor increase in power consumption.

Figure 7:
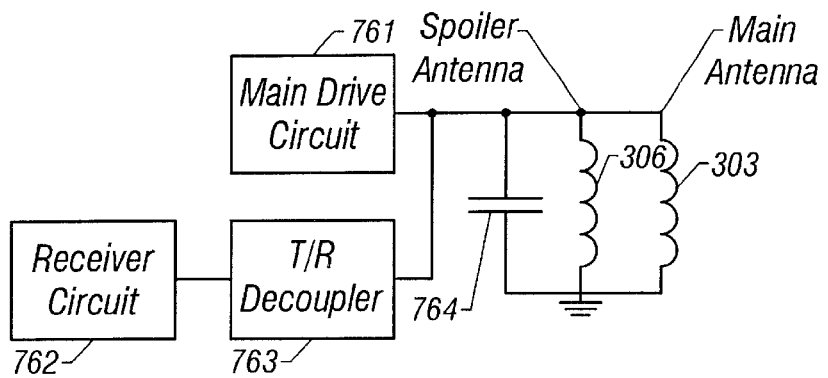
FIG. 7 is a schematic diagram for a permanently connected spoiler antenna in a preferred embodiment of the present invention.

Turning now to FIG. 7, a preferred embodiment of the present invention is illustrated in which the spoiler antenna 206 is permanently connected in parallel to the same drive circuit 761 as the main antenna. The receiver circuit 762 and transmit/receive decoupler 763 are shown for completeness. The spoiler antenna 206 can be connected in parallel with the main antenna 203 or in series. In the permanently connected configuration of FIG. 7, no additional drive circuitry dedicated to the spoiler antenna is not required. In particular only one capacitor 764 is used, as no extra capacitors are required to create the resonant circuit normally used to tune the resonant frequency of NMR antenna drive circuitry.

Figure 8:
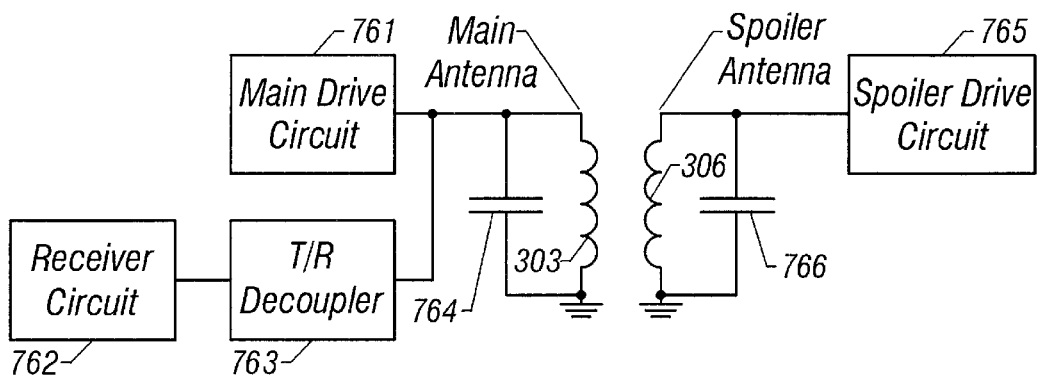
FIG. 8 is a schematic for an alternative embodiment of the present invention having an independent driver circuit for the spoiler antenna.

Turning now to FIG. 8, an alternative embodiment of the present invention is illustrated, wherein the performance of the spoiler antenna is significantly enhanced by selectively driving the spoiler antenna with a separate driver circuit 765, which enables selective driving of the spoiler antenna. The antenna drive circuitry 765 in the preferred NMR tool comprises a significant part of the tool design complexity, which increases the size and cost of a NMR tool. This is especially true in NMR tools that are designed to operate at multiple frequencies. To reduce power consumption to a minimum, the main RF antennas are tuned a desired resonant frequency utilizing a capacitor 764 in parallel or series with the antenna. In multiple frequency devices this capacitor is varied. With a separate antenna drive circuit, two circuits are tuned using capacitors 764 and 766. The separate drive configuration 765 is synchronized with the main drive circuit 761 to maintain the correct phase relationship between the main RF antenna 303 and the spoiler antenna 306. Antenna drive circuits 761 and 765 can be easily designed by persons familiar with the field of RF antenna circuit design.

The RF antenna drive circuit complexity is significantly reduced when the spoiler antenna is driven with the same drive circuitry as the main RF antenna, and the spoiler antenna is switched in and out of the circuit as desired.

Figure 9:
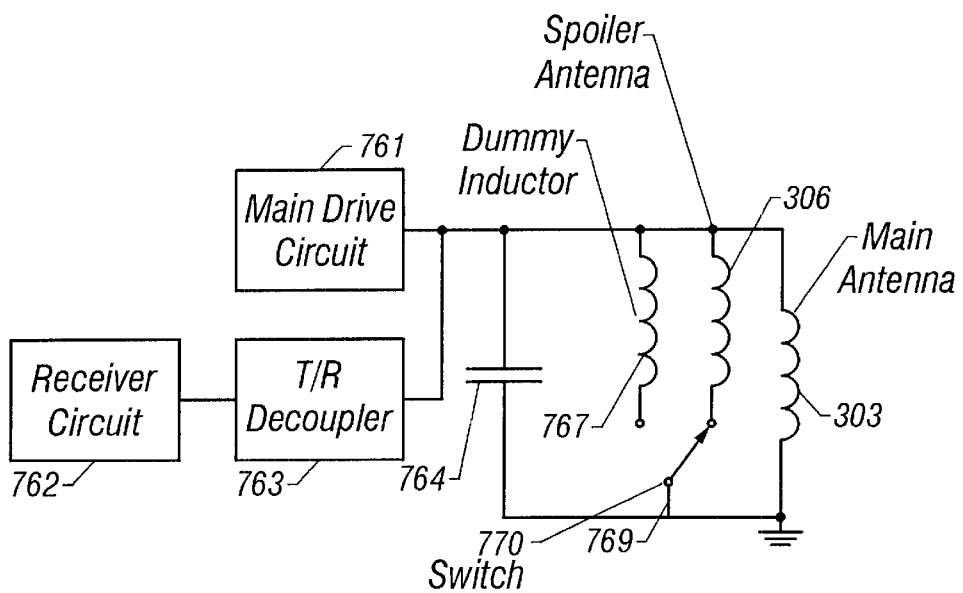
FIG. 9 is a schematic for a parallel switched spoiler antenna in an alternative embodiment of a preferred embodiment of the present invention.
Figure 10:
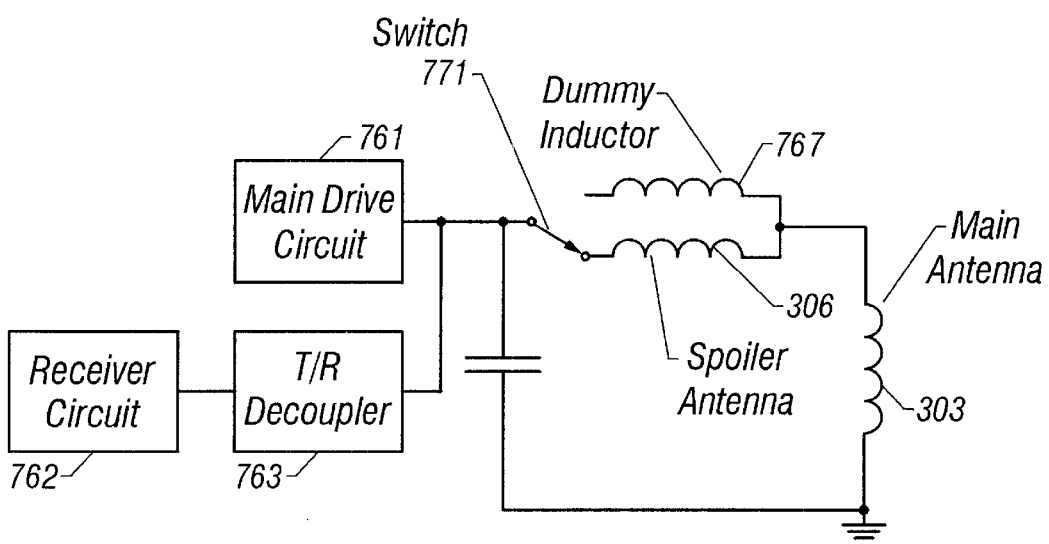
FIG. 10 is schematic for a series switched spoiler antenna for an alternative embodiment of a preferred embodiment of the present invention.

FIGS. 9,10 show alternative embodiments of the present invention in which the spoiler antenna is driven by the main RF antenna drive circuitry.

The spoiler and main antenna are tuned to a resonant frequency. When the spoiler antenna is switched in and out of the antenna drive circuit, it can change the inductance of the antenna driver circuit, and hence the resonant frequency of associated receiving antenna. It is preferable to maintain the inductance of the spoiler antenna at a level where this relative change is inductance is small when the spoiler antenna is removed from the circuit, so that a change in resonant frequency of the drive circuitry due to a change in inductance is negligible and can be ignored. In another alternative embodiment, a dummy antenna load inductor 769 having an impedance equal to the spoiler antenna 306, is provided so when the spoiler antenna is switched out of the driver circuit the dummy inductor is switched into the antenna driver circuit to maintain the inductance and resonant frequency of the main antenna when the spoiler is removed. FIGS. 9 illustrates such a switched system having a spoiler antenna 306 or dummy inductor 767 in the parallel with the main antenna 303 in a switched configurations. FIG. 10 illustrates a switched system having a spoiler antenna or dummy inductor in the series with the main antenna. Suitable switches 770, 771 may be used for the purpose.

The following table represents computer simulation results illustrating comparative NMR signal for various passive and active RF shields configurations and switching modes. The values in this table show the signal amplitude from the target region (in arbitrary units) and fractional sensitivity to a 12 inch borehole for an antenna design with the various shielding arrangements.

| Shield Type | Signal from Target Region (a.u.) | Fractional Borehole Sensitivity (%) |
| --- | --- | --- |
| No Shield | 18.2 | 4.8 |
| Internal, Passive Shield | 17.2 | 2.7 |
| External Shield 7 in. diameter | 16.3 | 0.5 |
| Active Spoiler for all transmitter pulses and in receive mode | 14.7 | 0.7 |
| Active spoiler for excitation pulse only | 16.2 | 0.4 |
| Active spoiler for excitation pulse and refocusing pulses | 15.9 | 0.1 |

Although the present invention has been described in terms of the foregoing embodiments, such description has been for exemplary purposes only, and, as will be apparent to those of ordinary skill in the art, may alternatives, equivalents, and variations of varying degrees will fall within the scope of the present invention. That scope, accordingly, is not limited in any respect by the foregoing description, but, rather, it is to be defined only by the claims which follow.

What is claimed is:

1. A side-looking nuclear magnetic resonance (NMR) sensing apparatus for operating in a bore hole to sense NMR signals emanating from a region of interest in a formation adjacent the bore hole, the tool comprising:

(a) a magnet for inducing a static magnetic field in the region of interest;

(b) a transmitting antenna assembly for inducing a radio frequency (RF) magnetic field in a first region including the region of interest;

(c) a receiving antenna assembly for receiving signals from a second region including the region of interest; and (d) a spoiler antenna assembly for spoiling the RF magnetic field so that the resultant RF field is forcefully mismatched to the static magnetic field in a portion of said second region outside the region of interest in order to reduce contributions to the sensed NMR signal therefrom, said portion including a portion of the bore hole.

2. The NMR apparatus of claim 1 wherein the spoiler antenna assembly is active only during a transmit period of the transmitting antenna assembly.

3. The NMR apparatus of claim 1 wherein the RF magnetic field comprises an excitation pulse and a plurality of refocusing pulses and the spoiler antenna assembly is active only dug the excitation pulse.

4. The NMR apparatus of claim 1 further comprising;
at least one switch for selectively disconnecting the spoiler antenna assembly from the transmitting and receiving antenna assembly during a selected time period.

5. The NMR apparatus of claim 1 wherein the transmitting antenna assembly is the same as the receiving antenna assembly.

6. The NMR apparatus of claim 5 wherein the spoiler antenna assembly is in series with the transmitting antenna assembly.

7. The NMR apparatus of claim 4 further comprising:
(i) a driver circuit for the transmitting antenna assembly, and
(ii) a switch for connecting to and disconnecting from the driver circuit a dummy inductor or the spoiler antenna assembly,
wherein the dummy inductor is connected to the driver circuit when the spoiler antenna assembly is disconnected from the driver circuit.

8. The NMR apparatus of claim 7 wherein the dummy inductor and the spoiler antenna assembly have substantially the same magnitude of inductance.

9. The NMR apparatus of claim 1 wherein the RF field is compensated so that the RF field near a resonance isoline of the static magnetic field in said portion is at least one of: (i) close to zero, or (ii) substantially parallel to the static magnetic field, thereby disrupting normal conditions for NMR excitation.

10. The NMR apparatus of claim 1 wherein the spoiler antenna assembly is permanently connected in parallel with the transmitting antenna assembly.

11. The NMR apparatus of claim 1 wherein the spoiler antenna assembly is connected to a drive circuit independent of a drive circuit for the transmitting antenna assembly.

12. The NMR apparatus of claim 1 wherein the spoiler antenna assembly is permanently connected in series with the transmitting RF antenna.

13. The NMR apparatus of claim 1 wherein the spoiler antenna assembly is selectively connected in series with the transmitting antenna assembly.

14. The NMR apparatus of claim 1 wherein the spoiler antenna assembly is selectively connected in parallel with the transmitting antenna assembly.

15. The NMP apparatus of claim 1 wherein at least one of the antenna assemblies further comprises a soft magnetic core.

16. A method of using a side-looking nuclear magnetic resonance (NMR) sensing apparatus in a bore hole to sense NMR signals emanating from a region of interest in a formation adjacent the bore hole, the method comprising:

(a) using a magnet on the sensing apparatus for inducing a static magnetic field in the region of interest;

(b) using a transmitting antenna assembly on the sensing apparatus for inducing a radio frequency (RF) magnetic field in a first region including the region of interest;

(c) using a receive antenna assembly for receiving signals from a second region including the region of interest; and (d) using a spoiler antenna assembly on the sensing apparatus for altering the RF magnetic field so that the resultant RF field is forcefully mismatched to the static magnetic field in a portion of said second region outside the region of interest to reduce contributions to the sensed NMR signal therefrom, said portion including a portion of the bore hole.

17. The method of claim 16 wherein the spoiler antenna assembly is active only during a transmit period of the transmitting antenna assembly.

18. The method of claim 16 wherein the RF magnetic field comprises an excitation pulse and a plurality of refocusing pulses and the spoiler antenna assembly is active only during the excitation pulse.

19. The method of claim 16 further comprising: using at least one switch for selectively disconnecting the spoiler antenna assembly from the transmitting antenna assembly during a selected time period.

20. The method of claim 16 wherein the transmitting antenna assembly is the same as the receiving antenna assembly.

21. The method of claim 20 wherein the spoiler antenna is in series with the transmitting antenna.

22. The method of claim 16, further comprising:
(i) using a driver circuit for driving the spoiler antenna, and
(ii) using a switch for connecting to and disconnecting from the driver circuit a dummy inductor or the spoiler antenna assembly,
wherein the dummy inductor is connected to the driver circuit when the spoiler antenna assembly is disconnected from the driver circuit.

23. The method of claim 22 wherein the dummy inductor and the spoiler antenna assembly have substantially the same magnitude of inductance, so that a resonant frequency for the driver circuit is substantially the same when the spoiler antenna assembly is connected to the driver circuit and when the dummy inductor is connected to the driver circuit.

24. The method of claim 16 wherein altering the RF field further comprises changing the RF field near a resonance isoline of the static magnetic field in the portion of said region outside the region of interest to one that is at least one of: (i) close to zero, or (ii) substantially parallel to the static magnetic field.

25. The method of claim 20 wherein the spoiler antenna assembly is permanently connected in parallel with the main RF antenna.

26. The method of claim 16 wherein the spoiler antenna assembly is connected to a drive circuit independent of a drive circuit for the transmitting antenna assembly.

27. The method of claim 16 wherein the spoiler antenna assembly is permanently connected in series with the transmitting RF antenna assembly.

28. The method of claim 16 wherein the spoiler antenna assembly is selectively connected in series with the transmitting antenna assembly.

29. The method of claim 16 wherein the spoiler antenna assembly is selectively connected in parallel with the transmitting antenna assembly.

30. The method of claim 16 further comprising providing a soft magnetic core to at least one of the antenna assemblies.

31. The method of claim 16 wherein the magnet has a magnetic dipole moment perpendicular to a line which passes through effective centers of the transmitting antenna assembly dipole moment and the spoiler antenna assembly dipole moment.

32. The NMR apparatus of claim 1 further comprising a driver circuit for activating the spoiler antenna assembly.

33. The NMR apparatus of claim 4 wherein said selected time period comprises a receive period of the receiving antenna assembly.

34. The NMR apparatus of claim 4 wherein said RF magnetic field comprises an excitation pulse and a plurality of refocusing pulses, and wherein said selected time period comprises a refocusing pulse.

35. The NMR apparatus of claim 1, wherein the spoiler antenna assembly is in series with and has an inductance that is relatively small compared to an inductance for the transmitting antenna assembly.

36. The method of claim 18 further comprising providing a driver circuit for activating the spoiler antenna assembly.

37. The method of claim 19 wherein said selected time period comprises a receive period of the transmitting antenna assembly.

38. The method of claim 19 wherein said RF magnetic field comprises an excitation pulse and a plurality of refocusing pulses, and wherein said selected time period comprises a refocusing pulse.

39. The NMR apparatus of claim 6 wherein the spoiler antenna assembly has an inductance that is relatively small compared to an inductance for the transmitting antenna assembly.

40. The NMR apparatus of claim 5 wherein the spoiler antenna assembly is in parallel with the transmitting antenna assembly.

41. The NMR apparatus of claim 1 wherein the magnet has a magnetic dipole moment perpendicular to a line which passes through effective centers of the transmitting antenna assembly dipole moment and the spoiler antenna assembly dipole moment.

42. The method of claim 21 wherein the spoiler antenna assembly has a inductance that is small compared to an inductance of the transmitting antenna assembly.

43. The method of claim 20 wherein the spoiler antenna assembly is in parallel with the transmitting antenna.

44. The method of claim 19 further comprising providing a driver circuit for activating the spoiler antenna assembly.

* * * * *